United States Patent [19]

Ghebre-Sellassie et al.

[11] Patent Number: 4,810,501
[45] Date of Patent: Mar. 7, 1989

[54] SUSTAINED RELEASE PHARMACEUTICAL PREPARATIONS

[75] Inventors: Isaac Ghebre-Sellassie, Stanhope; Russell U. Nesbitt, Jr., Somerville; Uma Iyer, Mendham; Mahdi B. Fawzi, Flanders, all of N.J.

[73] Assignee: Warner-Lambert Company, Morris Plains, N.J.

[21] Appl. No.: 875,146

[22] Filed: Jun. 17, 1986

[51] Int. Cl.⁴ .............................................. A01N 25/26
[52] U.S. Cl. ..................................... 424/469; 424/470
[58] Field of Search .................. 424/19, 490, 469, 470

[56] References Cited

U.S. PATENT DOCUMENTS

| 2,897,121 | 7/1959 | Wagner | 167/82 |
| 3,594,470 | 7/1971 | Borodkin et al. | 424/490 |
| 3,950,508 | 4/1976 | Mong et al. | 424/469 |
| 4,011,061 | 3/1977 | Forseen et al. | 424/19 |
| 4,284,444 | 8/1981 | Bernstein et al. | 156/60 |
| 4,308,251 | 12/1981 | Dunn et al. | 424/19 |
| 4,321,117 | 3/1982 | Kaetsu et al. | 204/159.16 |
| 4,600,645 | 7/1986 | Ghebre-Sellassie | 424/19 |

Primary Examiner—Joseph L. Schofer
Assistant Examiner—Peter F. Kulkosky
Attorney, Agent, or Firm—Howard Olevsky; Ronald A. Daignault

[57] ABSTRACT

Sustained release solid dosage forms—i.e., tablets, pellets, granules, and powders—can be made using a combination of polymeric and ionic particulate materials to modify release profiles, permeability and processability.

10 Claims, 1 Drawing Sheet

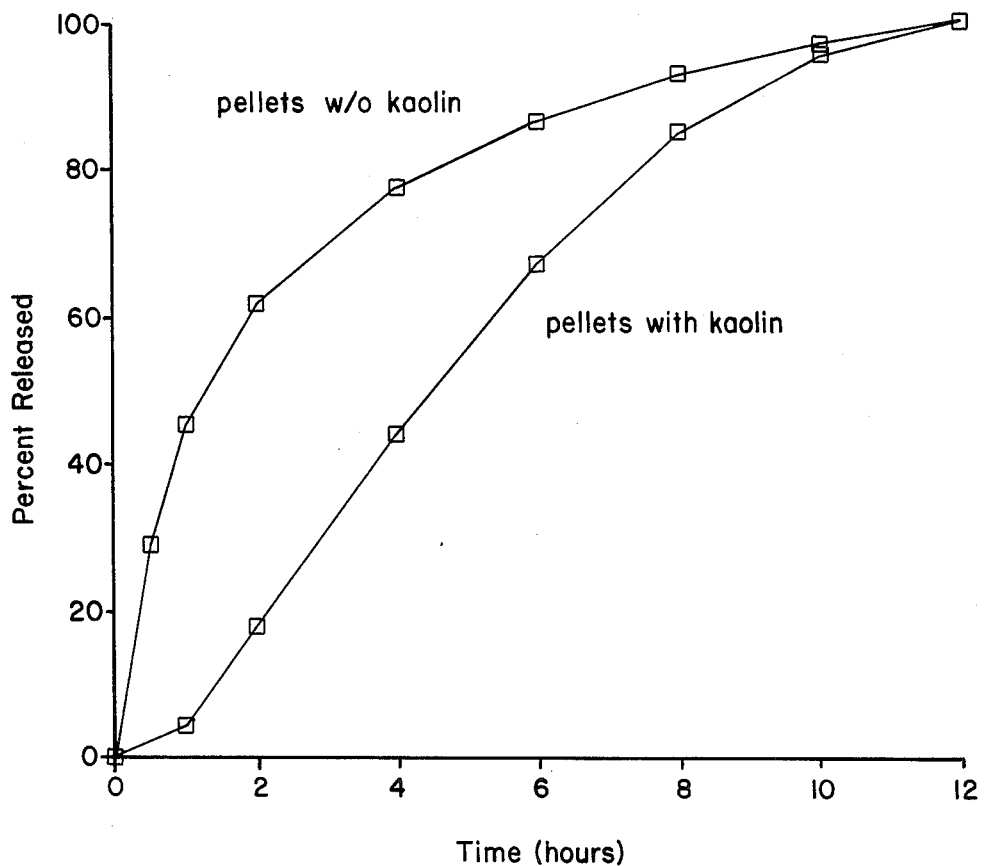

SUSTAINED RELEASE PHARMACEUTICAL PREPARATIONS

BACKGROUND

The treatment or coating of active substances, such as drugs, vitamins, minerals, and the like, has resulted in a variety of orally-administrable dosage forms. One principal goal in the formulation of such dosage forms is often the slow and sustained release of the active ingredient over a relatively long period of time, e.g., several hours. Such sustained release profiles generally afford such benefits as maximum dosage delivery with minimal compliance problems since, in the case of drugs, the patient need not take repeated dosages in order to ensure long-term drug release.

THE INVENTION

It has been discovered that solid preparations for the administration of pharmaceuticals and other active substances can be produced having sustained release properties when the drug or other active ingredient is treated in accordance with a process which comprises:
(1) contacting at least one active substance with at least one ionically neutral polymer and at least one ionic particulate material or adsorbent;
(2) producing a composite of particulate material and active substance in which ion pairs bond the active substance to the particulate material, or the active is adsorbed on the particulate material and neutral polymers form binders;
(3) coating the composite produced with a neutral polymer; and
(4) recovering the product of step (3).

The composite product made in accordance with the process of the invention is believed to be the result of adsorption and/or ionic bonding between the surfaces of the active substance, e.g., drug, and the particulate ionic material. The bonding is believed to be more electrostatic than chemical in nature since the chemical nature of none of the components has been shown to be altered.

ADVANTAGES

The process of the invention has several advantages over prior art methods of treating active substances. First, the products have beneficial release profiles. That is, drugs or other active ingredients are released into the system of the patient/consumer gradually over a period of up to several hours at a constant rate.

In addition, the permeability characteristics of the polymer-containing membranes can be modified by suitable adjustment of the ratio of the coating levels of the neutral polymer.

Other advantages and aspects of the invention will be made apparent by the following description.

DESCRIPTION OF THE INVENTION

The invention comprises the process as summarized above. In general, it can be said to reside in a method which calls for:
(1) contacting one or more drugs or other active substances with a particulate material which has ionic and/or adsorbent character,
(2) producing a composite of these three ingredients, which composite comprises:
  (a) the product of the interaction, presumably the electro-chemical bonding, between the surfaces of the particulate material and the active component;
  (b) a neutral polymer that acts as a binder, and
  (c) a neutral polymer which forms the membrane that partially controls the rate of release of the active component after ingestion; and
(3) recovering the product of step (2).

Drug release is believed to be controlled by desorption from the adsorbent or disassociation of the ion pair and the encasing membrane (i.e. the film coating).

ACTIVE SUBSTANCES

The active component or ingredient to be treated in accordance with the invention is a biologically active substance. A wide variety of active materials are contemplated. Chief among them are drugs or pharmaceuticals, vitamins, minerals and other psychological substances which have beneficial biological effects after ingestion.

The following is merely a sampling of the types of active substances which can be employed. Such substances include: acetylcholine, noradrenalin, serotonin, callicretin, gastrin, secretin, adrenalin, insulin, glucagon, ACTH, growth hormone, genadotropic hormone, oxytocin, vasopressin, thyroxin, testicular hormone (testosterone), ovarian hormone (estradiol), corpus luteum hormone, luteal hormone (progesterone), adrenocortical hormone, prostagladin, various antihistaminic agents, antihypertensives, vasodilators, vasoprotectors, stomachics and digestives, anti-diarrheals and intenstinal absorbers, contraceptives, antiphlogistic, acetysalicylic acid, ibuprofen, phenacetin, mefenamic acid, maproxen, tiaramide, indomethacin, vitamins, various enzymes, antitumor agents (bleomycin, sarcomycin, actinomycin D, cyclophosphamide, nitrogen mustard, triethylene thiophosphoramide, mercaptopurine, methotrexate, thorouracil, mitomycin C, carsinophilin, chromomycin A, 1-2(2-tetrahydro-furyl)-5-fluorouracil etc.), radiopharmaceuticals, antibiotics (streptomycins, chloramphenicols, tetracyclines, erythromycins, trichomycins, bacitracins, colistins, polymixins, gramicidins, penicillins, griseofulvins, etc.), sulfanilamide and its derivatives, antituberculosis drugs (TB preparations), antisyphilitics, antilep, various biological preparations (vaccines, antiserums, toxins and antitoxins, etc.) amebicides, anthelmintics, antaraxocs, (anticataract agents, antiglaucoma agents, etc.), various fish drugs, agricultural drugs, interferon, auxin, gibberelline, cytokinin, absinthic acid, other phytohormones, sex pheromone, aggregatien pheromone, alarm pheromone, trail pheromone, cast pheromone, other pheromones, and the like. Mixtures can be used.

The active ingredient will generally comprise about 0.001 to about 50 wt %, preferably about 0.001 to about 40 wt %, of the final dosage form, based on total weight.

NEUTRAL POLYMERIC MATERIALS

The binder of matrix portion of the composite made in accordance with the instant process is a polymeric material having no ionizable groups in its backbone or elsewhere in its structure. By "ionizable groups" is meant groups which, when present in appropriate vehicle(s), dissociate to furnish positively and negative charged species. One typical ionically neutral polymer is hydroxypropyl cellulose.

The coating polymers are derives from acrylic esters, cellulosics and polyvinyl esters and ethers and/or other functionally equivalent monomers. While the final polymers are essentially neutral, the presence of acid, salt or other moieties which do not significantly effect the ionic neutrality of the polymers is permissible.

Useful coating polymers are usually supplied as aqueous dispersions. They can also be solvent-based coating systems. The presence of one or more co-diluents is contemplated. However, dispersions containing water as the only diluent are preferred for safety reasons.

In the fianl dosage form, the polymeric material will comprise about 10 to about 50 wt %, preferably about 10 to about 40 wt %, based on total weight.

THE PARTICULATE IONIC MATERIAL

Useful particulate materials are those whose ionic character make them candidates for participation in the ion pair bonds or adsorption to be formed beween the surface of the active substance and the surface of the ionic particulate.

While particulate size is not critical, it is generally advisable to employ particles whose rheological properties in combination with the aqueous polymeric binder component render them suitable as components of slow-release cores for ingestible substances. Typically, the particulate materials used herein will have particle sizes of about 325 mesh or less, preferably about 400 mesh or less based on U.S. standard sieve.

The ionic particles used are generally either inorganic, e.g., minerals and clays, or organic, e.g., ion exchange resins, modified neutral polymers. Mixtures of any of these types are operable. Two or more of the same type can be used.

The particles are preferably either silicious materials, e.g., kaolin, kaolin clay, silica, mineral silicates, etc., or ionic organic materials, such as styrene copolymers bearing functional ionic groups, and the like. Examples of such ionic copolymers are the styrenedivinyl benzene copolymers bearing sulfonate, carboxylate, quaternary ammonium and/or amine substituents.

The ionic character of minerals and other useful silicious particles is generally associated with their pKa values in aqueous media. In general, kaolin and other clays or clay-like materials having a significant surface charge density will be operable.

While not desiring to be bound by any particular theory, Applicants believe that an electro-chemical bonding akin to, and possibly involving, adsorption occurs between the active ingredients and the ionic particulates.

In general, the quantities of ionic particulate materials to be employed will be such that the final dosage form will contain from about 20 to about 90 wt % and preferably about 30 to about 80 wt % of this ingredient.

Other excipients and ingredients conventionally employed in the oral formulations for the administration of biologically beneficial active substances can also be employed in the instant formulations.

DOSAGE FORMS

The method described herein is suitable for producing a variety of solid dosage/administration forms. Powders, pellets, granules, and tablets which contain one or more active ingredients and the requisite coating or membrane of particulate and polymer can be produced.

While solid products are preferred, semisolids and liquids can also be treated in accordance herewith.

PROCESSING TECHNIQUES

In general, any apparatus reasonably suited for handling materials and substances of the types described above can be used in carrying out the invention.

One preferred production scheme, from which a skilled artisan can extrapolate, would involve the following steps:

(a) Adsorbing active ingredient onto ionic particulate substrate or silicious material;

(b) Mixing the product of step (a) with polymeric binder;

(c) layering the suspension on solid inert material and (d) Encapsulating with neutral polymeric resin.

TYPICAL SCHEME

A typical process for the suspension layering of sugar seeds is demonstrated by the following:

Non pareil sugar seeds in the range of 14-16#were coated with a suspension of drug, kaolin and binder to produce extremely smooth spherical drug pellets. These pellets were subsequently coated with a polymer dispersion.

The procedure employed was:

Kaolin was suspended in water. Diphenhydramine HCl was adsorbed onto the kaolin of mixing with the kaolin suspension. To the drug/kaolin mixture, an aqueous binder solution of hydroxypropyl cellulose in water was added. The resultant suspension was sprayed at a rate of 1 ml/min onto a fluidizing bed of nonpareil sugar seeds to yield pellets.

The pellets were then coated with an aqueous polymeric dispersion of ethylcellulose (Aquacoat ®) and dried overnight at 40° C.

The release of drugs from the coated pellets was studied and found to follow zero order up to 90% drug depletion.

DRAWING

The FIGURE shows the release profile of the pellets discussed in the Example. The upper curve shows the profile for pellets without kaolin. The lower shows the profile for pellets with kaolin.

EXAMPLE 100 g of kaolin was mixed thoroughly with 500 g of deionized water. 50g of diphenhydramine HCl was dissolved in the suspension and stirred. 35 g of Klucel ® (hydroxy propyl cellulose) was dissolved in 165 g of deionized water and mixed with the suspension.

The mixture was sprayed onto 150 g 14–16 mesh nonpareil seeds. The drug layered pellets were coated with Aquacoat ® to a coating level of about 7%. The drug release from the water-layered pellets was compared with that from similarly coated diphenhydramine HCl pellets.

| Time HR | Layered pellets | Percent Drug Released Regular Pellets |
|---|---|---|
| 0.5 | — | 28.8 |
| 1 | 4.2 | 45.1 |
| 2 | 17.8 | 61.7 |
| 4 | 43.9 | 77.4 |
| 6 | 67.1 | 86.4 |
| 8 | 84.8 | 92.9 |
| 10 | 95.9 | 97.1 |

| Time HR | Layered pellets | Percent Drug Released Regular Pellets |
| --- | --- | --- |
| 12 | 100.0 | 100.0 |

Reasonable variations, such as those which would occur to a skilled artisan, can be made herein without departing from the scope of the invention.

We claim:

1. A process for treating a biologically active substance to prepare the substance for constant rate sustained release comprising:
   (a) adsorbing active ingredient onto either an ionic particulate substrate or silicious material;
   (b) mixing the product thus formed with a polymeric binder to form a suspension;
   (c) layering the suspension on solid inert material; to form a product
   (d) encapsulating the product formed with a polymeric resin.

2. The process of claim 1 wherein the particulate material is of acidic or basic character prior to step (a).

3. The process of claim 2 wherein the particulate material is selected from the group consisting of: kaolin, non-kaolin clay, ion exchange resins having acidic or basic character and mixtures thereof.

4. The process of claim 1 wherein the particulate material is kaolin.

5. The process of claim 1 wherein the neutral polymeric binder is selected from the group consisting of cellulosic ethers, acrylics, and polyvinyl esters.

6. The process of claim 4 wherein the neutral polymer is a water insoluble aqueous polymer selected from the group consisting of acrylic resins, cellulosics, and polyvinyl esters.

7. The process of claim 6 wherein the polymer is supplied as an aqueous dispersion containing a copolymer derived from monomers selected from acrylic esters, methacrylic esters, and mixtures thereof.

8. The process of claim 1 wherein the particulate material is an ion-exchange resin having acidic or basic character.

9. The process of claim 8 wherein the ion exchange resin contains at least one ionic group selected from the group consisting of sulfonates, carboxylates, quaternary ammonium groups, amine groups, and mixtures thereof.

10. The process of claim 9 wherein the ion exchange resin is strongly acidic.

* * * * *